(12) United States Patent
Prystowsky et al.

(10) Patent No.: US 8,945,019 B2
(45) Date of Patent: *Feb. 3, 2015

(54) SYSTEM AND METHOD FOR PROCESSING AND PRESENTING ARRHYTHMIA INFORMATION TO FACILITATE HEART ARRHYTHMIA IDENTIFICATION AND TREATMENT

(75) Inventors: Eric N. Prystowsky, Carmel, IN (US); Lev Korzinov, San Diego, CA (US); Eric Baumann, San Diego, CA (US); Scott Denis, Murrieta, CA (US); Manuel E. Jaime, Solana Beach, CA (US); Justin James, San Diego, CA (US)

(73) Assignee: Braemar Manufacturing, LLC, Eagan, MN (US)

( * ) Notice: Subject to any disclaimer, the term of this patent is extended or adjusted under 35 U.S.C. 154(b) by 898 days.

This patent is subject to a terminal disclaimer.

(21) Appl. No.: 13/046,673

(22) Filed: Mar. 11, 2011

(65) Prior Publication Data

US 2011/0166468 A1 Jul. 7, 2011

Related U.S. Application Data

(63) Continuation of application No. 11/739,037, filed on Apr. 23, 2007, now Pat. No. 7,907,996, which is a continuation of application No. 10/760,122, filed on Jan. 16, 2004, now Pat. No. 7,212,850.

(60) Provisional application No. 60/525,386, filed on Nov. 26, 2003.

(51) Int. Cl.
*A61B 5/00* (2006.01)
*A61B 5/0245* (2006.01)
(Continued)

(52) U.S. Cl.
CPC .............. *A61B 5/0006* (2013.01); *A61B 5/0245* (2013.01); *A61B 5/046* (2013.01); *A61B 5/044* (2013.01)
USPC .......................................................... 600/508

(58) Field of Classification Search
CPC ....................................... A61B 5/0452–5/0472
USPC ................................................... 600/508–525
See application file for complete search history.

(56) References Cited

U.S. PATENT DOCUMENTS 4,173,971 A 11/1979 Karz
4,339,800 A * 7/1982 Woods ........................... 600/515
(Continued)

FOREIGN PATENT DOCUMENTS

EP 360412 B1 3/1995
JP 4300523 A 10/1992
(Continued)

OTHER PUBLICATIONS

Japanese Patent Application No. 2009-226039, Dispatch Date Sep. 20, 2011, Notification of Reason(s) for Refusal, with translation, 6 pages.
(Continued)

*Primary Examiner* — Scott Getzow
(74) *Attorney, Agent, or Firm* — Ropes & Gray LLP (57) ABSTRACT

A system and method for presenting information relating to heart data can involve operations including identifying arrhythmia events in physiological data obtained for a living being, receiving human assessments of at least a portion of the arrhythmia events, determining a measure of correlation between the human assessments and the identified events, and selectively presenting information regarding the identified events based on the measure of correlation. The operations can also include identifying atrial fibrillation events in physiological data obtained for a living being, obtaining heart rate data for the living being, and presenting information regarding the heart rate data and duration of the atrial fibrillation events together with a common time scale to pictographically represent heart rate trend with atrial fibrillation burden during a defined time period.

21 Claims, 6 Drawing Sheets

(51) Int. Cl.
*A61B 5/046* (2006.01)
*A61B 5/044* (2006.01)

(56) References Cited

U.S. PATENT DOCUMENTS

| | | | |
|---|---|---|---|
| 4,622,979 | A | 11/1986 | Katchis et al. |
| 4,630,204 | A | 12/1986 | Mortara |
| 4,920,489 | A | 4/1990 | Hubelbank et al. |
| 4,938,228 | A | 7/1990 | Righter et al. |
| 4,951,681 | A | 8/1990 | Mortara |
| 4,958,641 | A | 9/1990 | Digby et al. |
| 4,977,899 | A | 12/1990 | Digby et al. |
| 5,191,891 | A | 3/1993 | Righter |
| 5,197,479 | A | 3/1993 | Hubelbank et al. |
| 5,217,021 | A | 6/1993 | Steinhaus et al. |
| 5,226,425 | A | 7/1993 | Righter |
| 5,365,935 | A | 11/1994 | Righter et al. |
| 5,421,342 | A | 6/1995 | Mortara |
| 5,490,515 | A | 2/1996 | Mortara |
| 5,513,645 | A | 5/1996 | Jacobson et al. |
| 5,522,396 | A | 6/1996 | Langer et al. |
| 5,546,950 | A | 8/1996 | Schoeckert et al. |
| 5,581,369 | A | 12/1996 | Righter et al. |
| 5,634,468 | A | 6/1997 | Platt et al. |
| 5,676,153 | A | 10/1997 | Smith et al. |
| 5,678,562 | A | 10/1997 | Sellers |
| 5,704,351 | A | 1/1998 | Mortara et al. |
| 5,730,143 | A | 3/1998 | Schwarzberg |
| 5,868,680 | A | 2/1999 | Steiner et al. |
| 5,931,791 | A | 8/1999 | Saltzstein et al. |
| 5,942,986 | A | 8/1999 | Shabot et al. |
| 5,966,692 | A | 10/1999 | Langer et al. |
| 6,064,906 | A | 5/2000 | Langberg et al. |
| 6,102,856 | A | 8/2000 | Groff et al. |
| 6,246,907 | B1 | 6/2001 | Lin et al. |
| 6,287,252 | B1 | 9/2001 | Lugo |
| 6,302,844 | B1 | 10/2001 | Walker et al. |
| 6,366,871 | B1 | 4/2002 | Geva |
| 6,409,661 | B1 | 6/2002 | Murphy |
| 6,411,840 | B1 | 6/2002 | Bardy |
| 6,418,340 | B1 | 7/2002 | Conley et al. |
| 6,449,504 | B1 | 9/2002 | Conley et al. |
| 6,485,429 | B2 | 11/2002 | Forstner |
| 6,490,479 | B2 | 12/2002 | Bock |
| 6,524,239 | B1 | 2/2003 | Reed et al. |
| 6,564,077 | B2 | 5/2003 | Mortara |
| 6,583,796 | B2 | 6/2003 | Jamar et al. |
| 6,609,023 | B1 | 8/2003 | Fischell et al. |
| 6,648,827 | B2 | 11/2003 | Heikkilä et al. |
| 6,665,558 | B2 * | 12/2003 | Kalgren et al. ............... 600/510 |
| 6,687,685 | B1 | 2/2004 | Sadeghi et al. |
| 6,697,655 | B2 | 2/2004 | Sueppel et al. |
| 6,937,887 | B2 * | 8/2005 | Bock ............................ 600/519 |
| 7,001,334 | B2 | 2/2006 | Reed et al. |
| 7,223,234 | B2 | 5/2007 | Stupp et al. |
| 7,311,665 | B2 | 12/2007 | Hawthorne et al. |
| 7,542,878 | B2 | 6/2009 | Nanikashvili |
| 2002/0099303 | A1 | 7/2002 | Bardy |
| 2002/0128804 | A1 * | 9/2002 | Geva ............................. 702/188 |
| 2002/0143266 | A1 | 10/2002 | Bock |
| 2002/0173727 | A1 | 11/2002 | Bardy |
| 2003/0028442 | A1 | 2/2003 | Wagstaff et al. |
| 2003/0069486 | A1 | 4/2003 | Sueppel et al. |
| 2003/0069487 | A1 | 4/2003 | Mortara |
| 2004/0010201 | A1 | 1/2004 | Korzinov et al. |
| 2005/0119833 | A1 | 6/2005 | Nanikashvili |
| 2005/0203349 | A1 | 9/2005 | Nanikashvili |
| 2007/0100213 | A1 | 5/2007 | Dossas et al. |

FOREIGN PATENT DOCUMENTS

| | | |
|---|---|---|
| JP | 6399840 A | 5/1998 |
| JP | 10243930 A | 9/1998 |
| JP | 2000195910 A | 7/2000 |
| JP | 2003000559 A | 1/2003 |
| JP | 2003130815 A | 5/2003 |
| WO | WO0176461 A3 | 1/2002 |
| WO | WO0224276 A1 | 3/2002 |

OTHER PUBLICATIONS

Japanese Patent Application No. 2010-05641, Dispatch Date Sep. 20, 2011, Notification of Reason(s) for Refusal, with translation, 6 pages.
Jan Galuszka et al., "Assessment of Spectral Analysis of Heart Rate Variability in Patients With History of Atrial Fibrillation by Means of Age-Dependent Parameters", Biomed. Papers 146(2), 81-85 (2002).
Med Monitoring Systems, Inc. (Holter, Spiro, DMS, ECG, EKG, APB), http://www.medmonitoringsystems.com/holtertestanalysis2.html [Retrieved Nov. 13, 2003].
Massimo Santini et al., "Atrial Fibrillation: The Role of Atrial Defibrillation", Journal of Interventional Cardiac Electrophysiology 9, 229-233, 2003.
Australian Patent Office, Application No. 2004305423, in office action mailed Nov. 23, 2007, 2 pages.
Canadian Intellectual Property Office, Application No. 2,544,926, mailed Mar. 10, 2008, 3 pages.
Jun. 30, 2009, JP Office Action for patent application No. 2006-541106.
Japanese Patent Application No. 2006-541106, Dispatch Date Nov. 4, 2009, Notification of Reason(s) for Refusal, with translation, 7 pages.
Biomedical Computer Laboratory, Institute for Biomedical Computing, Washington University, "Progress Report No. 21," Jul. 1, 1984-Jun. 30, 1985, 164 pages.
Savi Wireless 0 Mobile Cardiac Telemetry Brochure, published by at least May 2009, 12 pages, Medicomp, Melbourne, Florida.
Canadian Intellectual Property Office, Application No. 2,544,926, mailed Apr. 7, 2009, 3 pages.
Getzow, Scot M., Authorized Officer, International Searching Authority, Application No. PCT/US04/01107, filed Jan. 16, 2005.
Mar. 10, 2008, CA2544926; Office Action From CA Intellectual Property Office, (CA counter-part).
Jun. 20, 2009, JPO Office Action for patent application No. 2006-541106.
Japanese Patent Office, Nov. 4, 2009, Office Action for Application No. JP2006-5411006.
European Patent Office, Application No. 04702945.9, filed Jan. 16, 2004, in Supplementary Partial European Search Report, mailed Nov. 11, 2010, 4 pages.
Japanese Patent Application No. 2006-541106, Dispatch date May 18, 2010, Decision of Refusal, 9 pages, including translation.
Canadian Intellectual Property Office, Application No. 2544926, filed Apr. 28, 2006, in Office Action dated Jun. 22, 2011, 2 pages.

* cited by examiner

SYSTEM AND METHOD FOR PROCESSING AND PRESENTING ARRHYTHMIA INFORMATION TO FACILITATE HEART ARRHYTHMIA IDENTIFICATION AND TREATMENT

CROSS REFERENCE TO RELATED APPLICATIONS

This application is a continuation application of and claims the benefit of priority to U.S. application Ser. No. 11/739,037 filed on Apr. 23, 2007, which is a continuation of U.S. Pat. No. 7,212,850 (application Ser. No. 10/760,122) issued on May 1, 2007 and filed on Jan. 16, 2004, which is a non-provisional of 60/525,386, filed on Nov. 26, 2003. The disclosure of the prior applications is considered part of and is incorporated by reference in the disclosure of this application.

BACKGROUND

The present application describes systems and techniques relating to processing and presenting arrhythmia event information from physiological data, for example, selectively presenting atrial fibrillation events to a medical practitioner.

Over the years, various devices have been used for monitoring hearts in living beings. Additionally, systems have been used to collect and report on heart information obtained from patients.

SUMMARY

In general, in one aspect, a heart monitoring system collects heart data from a monitored individual and stores the data at a monitoring center. Collected data can be processed, and graphical representations of the collected information can be presented to medical practitioners to assist in treating heart arrhythmias, such as atrial fibrillation. A system and method can involve operations including identifying arrhythmia events in physiological data obtained for a living being, receiving human assessments of at least a portion of the arrhythmia events, determining a measure of correlation between the human assessments and the identified events, and selectively presenting information regarding the identified events based on the measure of correlation. The operations also can include identifying atrial fibrillation events in physiological data obtained for a living being, obtaining heart rate data for the living being, and presenting information regarding the heart rate data and duration of the atrial fibrillation events together with a common time scale to pictographically represent heart rate trend with atrial fibrillation burden during a defined time period.

One or more of the following advantages can be realized. The heart monitor can loop every twenty-four hours and can automatically transmit heart data at least every twenty-four hours. The system can automatically generate a daily graphical summary of atrial fibrillation (AF) burden for review by a medical practitioner, which can be presented effectively anywhere using one or more communication networks. The AF burden graph can be used for asymptomatic AF detection, drug therapy (rate, rhythm, anti-coagulants), pre/post ablation monitoring, and CHF (congestive heart failure) decompensation. The system can provide an overall sensitivity of 96%, a positive predictivity of over 99%, and artifact rejection of over 90%. In one implementation, the graph only displays events where AF detection is validated by a technician finding AF in over 50% of the automatically identified events.

The details of one or more embodiments are set forth in the accompanying drawings and the description below. Other features and advantages will become apparent from the description, the drawings, and the claims.

DETAILED DESCRIPTION

Figure 1:
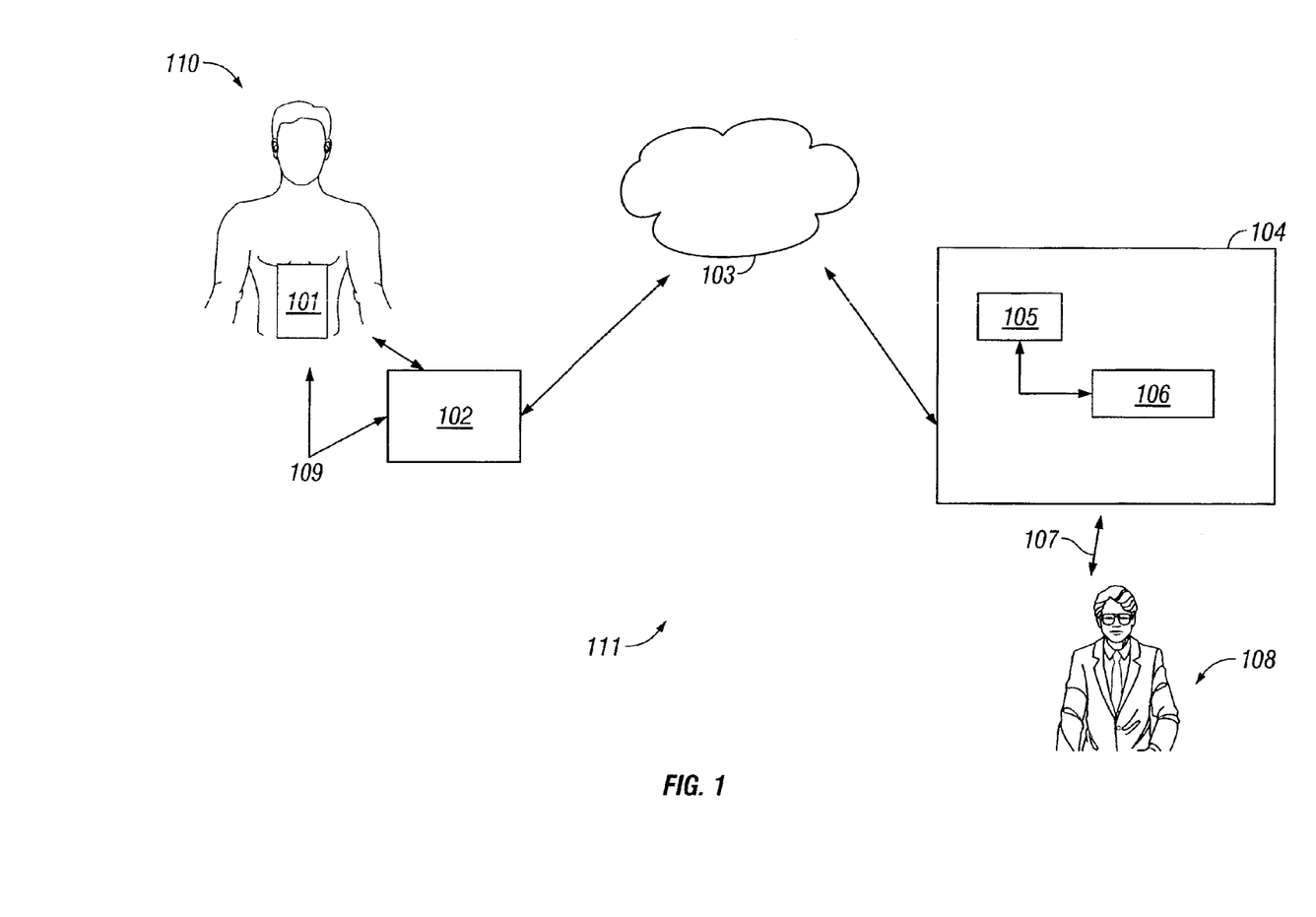
FIG. 1 illustrates, according to an exemplary embodiment, a system for reporting information related to arrhythmia events.

FIG. 1 illustrates, according to one embodiment, a system for reporting information related to arrhythmia events, such as atrial fibrillation events. In this embodiment, monitoring system 109 can communicate (via devices 101 and 102) ECG (electrocardiogram), cardiac event, and other data to monitoring center 104. The system 109 can include, for example, an implantable medical device (IMD), such as an implantable cardiac defibrillator and an associated transceiver or pacemaker and an associated transceiver, or a monitoring device 101 that a patient 110 wears. Further, monitoring system 109 can include a monitor processing device 102 that can send standard physiological data (received from monitoring device 101) to monitoring center 104 and that can detect arrhythmia events (such as atrial fibrillation events). In one implementation, the devices 101 and 102 are integrated into a single device. Moreover, the system 109 can be implemented using, for example, the CardioNet Mobile Cardiac Outpatient Telemetry (MCOT) device, which is commercially available and provided by CardioNet, Inc of San Diego, Calif.

Monitor processing device 102 can transmit physiological data (including data related to arrhythmia events) through a communication network 103, which can be a local area network (LAN), a landline telephone network, a wireless network, a satellite communication network, or other suitable network to facilitate two-way communication with monitoring center 104. Advantageously, monitoring center 104 can be located in the same location (e.g., in the same room or building) as monitoring system 109 or at some remote location.

The monitoring center 104 can include a monitoring (or display) station 105 and a processing system 106. In one implementation, a cardiovascular technician (CVT) can use the monitoring station 105 to evaluate physiological data received from monitoring system 109, identifying and reporting, among other things, arrhythmia events (such as atrial fibrillation events). The CVT reports these assessments of the physiological data to the processing system 106, which also receives information related to the arrhythmia events identified by monitoring system 109. As will be explained further below, processing system 106 analyzes this arrhythmia event data (both the human-assessed data from the CVT and the data reported by monitoring system 109) and determines whether to generate a graph (or other similar presentation) related to these events. In certain circumstances, the processing system will send a report related to both arrhythmia and heart rate data to, for example, a physician or other health care provider 108 via transmission path 107—which may be part of the network 103.

Figure 3:
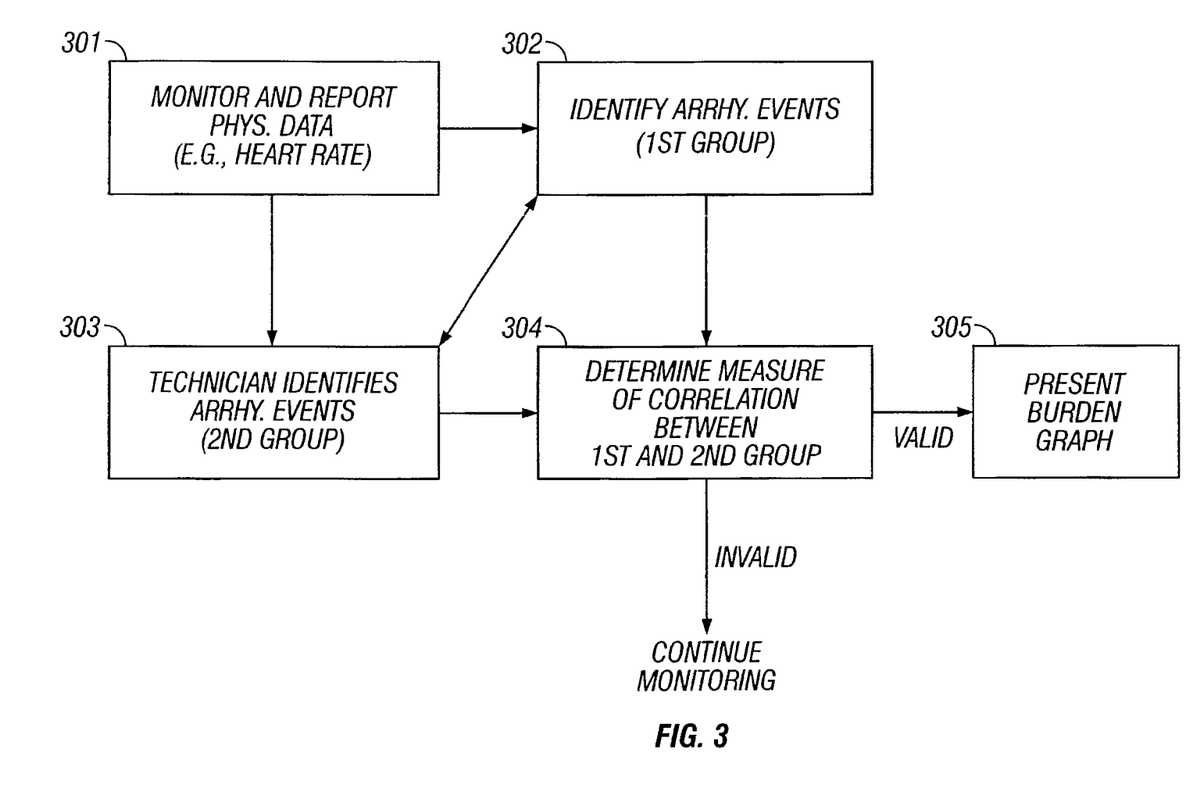
FIG. 3 is a diagram illustrating, according to an exemplary embodiment, a procedure for monitoring, processing, and reporting information related to arrhythmia events.

FIG. 3 illustrates, according to one embodiment, a procedure for monitoring, processing, and reporting arrhythmia event data (such as data associated with atrial fibrillation events). In this embodiment, the monitoring system 109 (illustrated in FIG. 1) monitors and reports physiological data (including data related to heart rate) at 301. At 302, various parts of this physiological data can be analyzed (for example, RR variability and QRS morphology) and arrhythmia events can be identified based on predefined criteria—the information relating to these events (among other possible information) constituting a first group of data. In one implementation, the monitoring system 109 identifies certain of the arrhythmia events that are urgent or representative and reports those events to both a CVT at 303 and to the processing system at 304. Alternatively, the system could simply report the events identified at 302 to the processing system. Further, at 303, a CVT, using station 105, evaluates various parts of the physiological data received from 302 and/or 301 and also identifies arrhythmia events—the information relating to these human-assessed events (among other possible information) constituting a second group of data. Here, if needed, the CVT can request additional data from monitoring system 109.

At 304, the processing system 106 analyzes both the first and second group of data, determining a measure of correlation between these groups. This process can involve, for example, determining whether a correlation measure exceeds and/or equals a predetermined correlation parameter or whether a correlation measure is less than and/or equals that parameter. If, based on the correlation analysis, the information related to the arrhythmia events is determined to be valid, then the system generates a report relating to both heart rate trend and the arrhythmia events at 305, such as the graph shown in FIG. 2 or the graphs shown in FIG. 4. If, on the other hand, there is insufficient correlation, then the system does not generate a report and monitoring continues.

To illustrate, in one implementation, every ten minutes, the monitoring system 109 transmits a "flag" if it has detected an atrial fibrillation (AF) event in the last ten minutes. In this implementation, the processing system 106 only generates a graph (or graphs) related to heart rate trend and atrial fibrillation burden—such as the graph shown in FIG. 2 or the graphs shown in FIG. 4—if more than 50% of the ten minute flags (generated at 302) match events identified by a CVT (at 303)—a correlation (with respect to the time period at issue) indicating a high positive predictivity for the identification of AF events. If this 50% threshold is not met, then the system does not generate a graph (or graphs) based on the data at issue and simply continues to process data.

The term "atrial fibrillation burden" (or more generally, "arrhythmia event burden") refers generally to the overall amount of time that a patient is in atrial fibrillation (or arrhythmia) over a specified time period, taking into account the number and duration of episodes. Advantageously, employing pictographic presentations, such as those of FIGS. 2 and 4, a medical practitioner can see whether a patient is more likely to experience an arrhythmia, such as AF, at certain times of the day, and this can affect therapeutic approaches in some cases.

Figure 2:
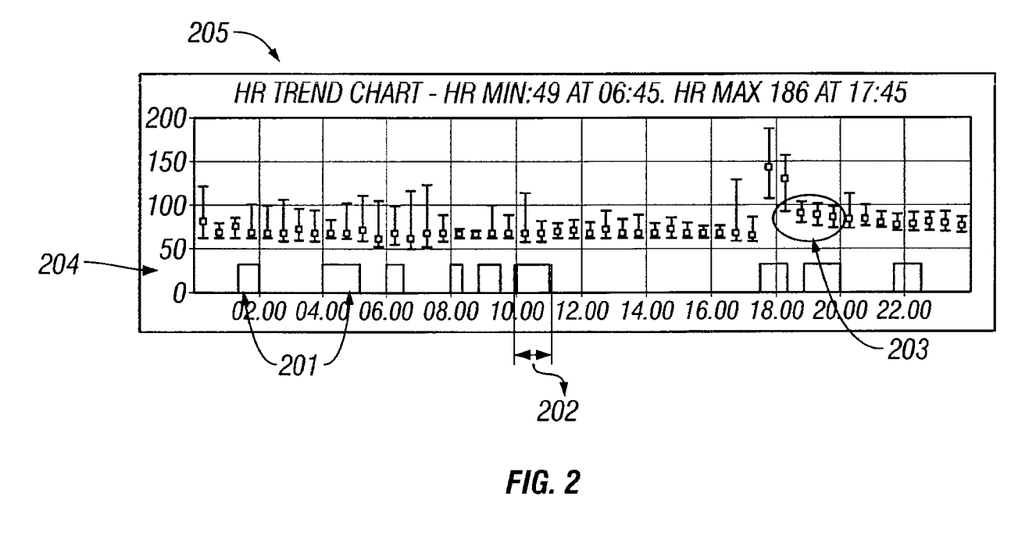
FIG. 2 shows, according to one embodiment, a graph presenting an example of atrial fibrillation burden and heart rate trend.

FIG. 2 represents one example of how to pictographically present both heart rate trend and atrial fibrillation burden on a common time scale (to "pictographically present" such data, however, a graph is not required.). The graph 205 contains information relating to, for example, daily AF incidence and time of occurrence 201, AF duration 202, and heart rate (203 and 204). A scale 204 (in this example) indicates heart rate in average beats-per-minute and the dots and lines shown at 203 (for example) indicate values on that scale, standard deviations associated with these values, and heart rates during AF. Further, graph 205 shows heart rate data at 15 minutes and 45 minutes past the hour. Finally, in this graph, the presence of one or more AF events in a given 10-minute period is graphed as a 10-minute interval.

Figure 4:
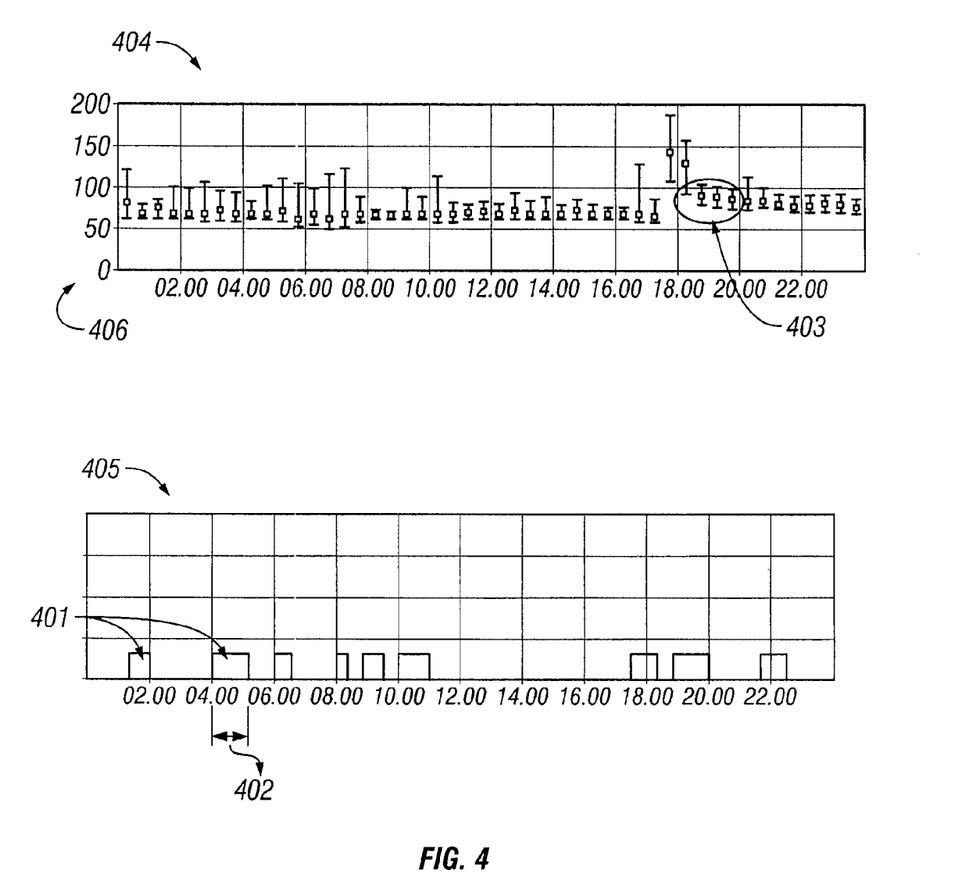
FIG. 4 shows, according to an exemplary embodiment, one graph presenting an example of atrial fibrillation burden and one graph presenting an example of heart rate trend.

Like FIG. 2, FIG. 4 represents an example of how to pictographically present heart rate trend and atrial fibrillation burden on a common time scale. Although FIG. 4, unlike FIG. 2, uses two graphs, FIG. 4 presents the same information as FIG. 2. Specifically, graphs 404 and 405 contain information relating to, for example, daily AF incidence and time of occurrence 401, AF duration 402, and heart rate (403 and 406). A scale 406 (in this example) indicates heart rate in average beats-per-minute and the dots and lines shown at 403 (for example) indicate values on that scale, standard deviations associated with these values, and heart rates during AF.

Figure 5:
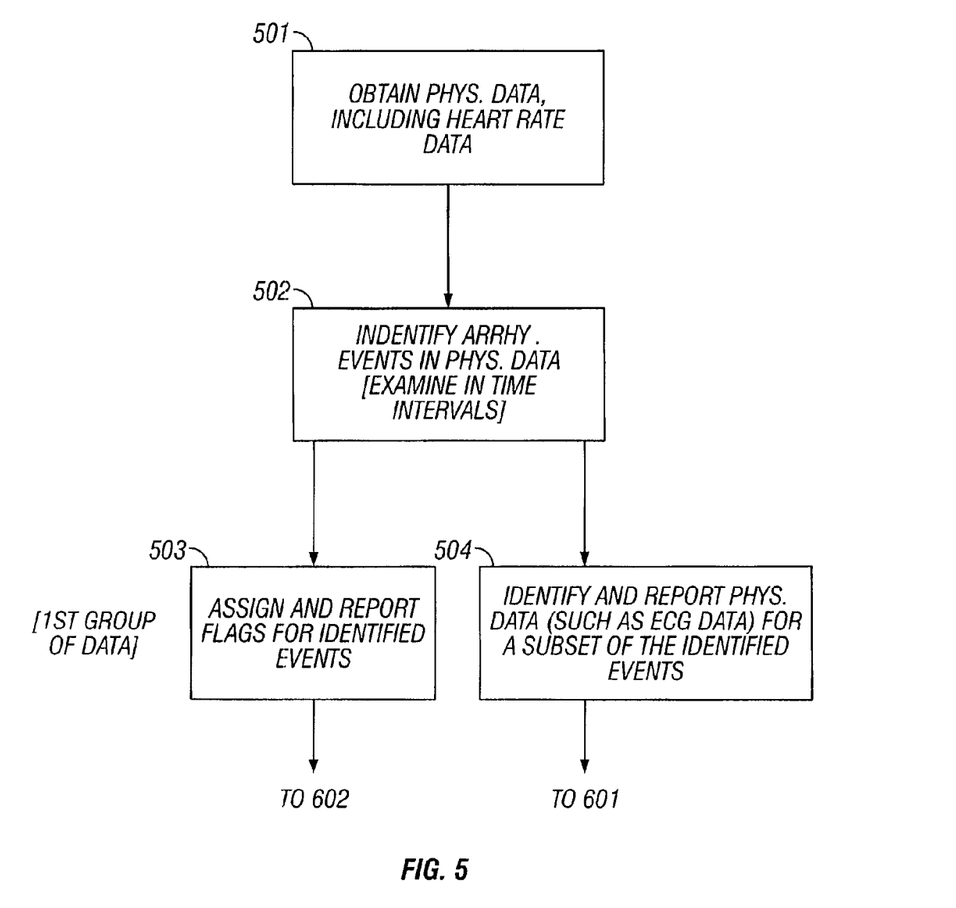
FIGS. 5 and 6 are diagrams illustrating, according to another exemplary embodiment, a procedure for monitoring, processing, and reporting information related to arrhythmia events.
Figure 6:
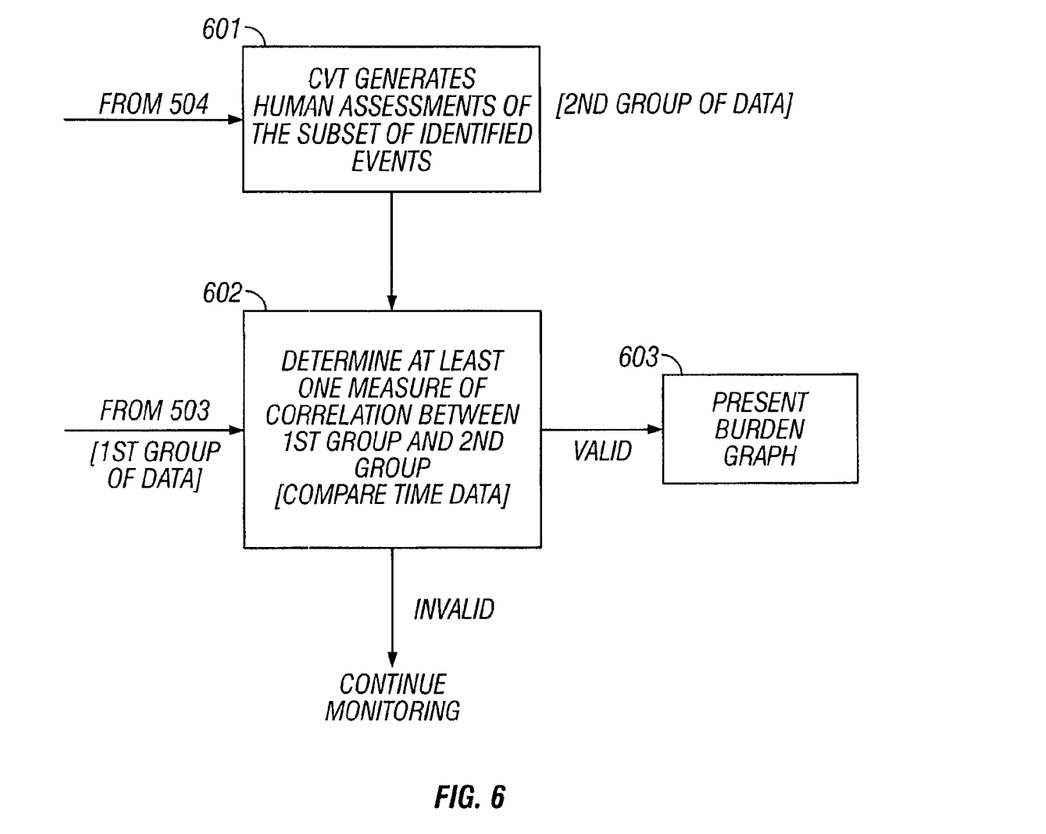

FIGS. 5 and 6 are diagrams illustrating another implementation of the invention. Specifically, at 501, the system 111, employing monitoring system 109, obtains physiological data, including heart rate data. In turn, at 502, the system identifies the presence of arrhythmia events (such as AF events) in this physiological data, examining this data in time intervals. At 503, the system assigns flags indicating the presence of arrhythmia events and reports those flags—which represent a first group of data—to the processing system. Similarly, at 504, the system identifies and reports physiological data, such as ECG data, for a subset of the events identified at 502 and reported at 503. Notably, the system, in this implementation, need not report physiological data for each flag assigned at 503, but need only report data associated with the most significant events identified at 502, thereby minimizing the data sent to a CVT.

At 601, the CVT analyzes this data and reports whether arrhythmia events have occurred, thereby generating a second group of data. The processing system then determines (at 602), based on comparing time stamps associated with each group of data, at least one measure of correlation between the first group of data and the second group of data. To illustrate, if enough of the human-assessed events reported at 601 match the events reported at 503, then the system determines that the data is valid, that is, that there is a high positive predictivity for the identification of arrhythmia events. If such a determination is made, the data associated with each flag reported at 503 is pictographically presented in a form such as FIG. 2 or FIG. 4. Significantly, in this implementation, while this pictographic representation can contain all such data, the CVT need only review a subset of this data. In short, the system achieves increased accuracy in the presentation of information relating to arrhythmia events while minimizing the data that the CVT reviews.

The disclosed system and all of the functional operations described and illustrated in this specification can be implemented in digital electronic circuitry, or in computer hardware, firmware, software, or in combinations of the forgoing. Apparatus can be implemented in a software product (e.g., a computer program product) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

To provide for interaction with a user (such as the CVT), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

Finally, while the foregoing system has been described in terms of particular implementations, other embodiments are within the scope of the following claims. For example, the disclosed operations can be performed in a different order and still achieve desirable results. Moreover, the system need not employ 10-minute intervals; many different time intervals are possible (as is no interval at all), including 1 minute, 30 second, and 30-minute intervals. Indeed, because time intervals are not required, the graphs of FIGS. 2 and 4 could be modified to show continuous heart rate trend (accompanied by corresponding AF data) rather than just specific instances of this trend. Further, while FIGS. 2 and 4 show examples of (among other things) pictographically presenting atrial fibrillation burden (one type of arrhythmia event burden), one could present the same or similar information for another type of arrhythmia event. In fact, one could employ both the format and procedures associated with generating FIG. 2 or FIG. 4 (or a similar figure) to pictographically present information related to a number of different types of arrhythmia event burdens.

What is claimed is:

1. A method comprising:
obtaining data associated with multiple arrhythmia events identified, according to a computer implemented process, in a physiological signal for a living being;
receiving a human assessment of a portion of the data associated with a corresponding portion of the multiple arrhythmia events identified in the physiological signal;
determining that the multiple arrhythmia events identified in the physiological signal, including events not in the human assessed portion of the data, are valid when a threshold of the arrhythmia events identified according to the computer implemented process in the physiological signal in the human assessed portion of the data, match events identified by the human assessment of the human assessed portion of the data; and
generating information for a report to present the valid arrhythmia events for a defined period of time.

2. The method of claim 1, wherein obtaining the data associated with the multiple arrhythmia events identified according to the computer implemented process, in the physiological signal comprises obtaining ECG data.

3. The method of claim 2, wherein generating the information for the report comprises generating information for a pictographic report presenting on a common time scale heart rate trend in alignment with indications of the valid arrhythmia events.

4. The method of claim 2, wherein generating the information for the report comprises generating information for a pictographic report presenting a range of heart rates and a heart rate average for each of multiple time intervals juxtaposed with an indication of intervals of the multiple time intervals that correspond to the valid arrhythmia events.

5. The method of claim 4, further comprising providing the information over a network for displaying the report.

6. The method of claim 4, wherein generating the information for the report comprises generating information for presenting on the pictographic report an indication of a time interval of the multiple time intervals having a minimum heart rate for the multiple time intervals.

7. The method of claim 6, wherein generating the information for the report comprises generating information for presenting on the pictographic report an indication of a time interval of the multiple time intervals having a maximum heart rate for the multiple time intervals.

8. A system comprising:
a mobile monitoring system comprising a sensor to obtain physiological data from a living being, the mobile monitoring system configured to identify multiple arrhythmia events in the physiological data; and
a monitoring center in two-way communication with the mobile monitoring system via a network to obtain the physiological data, the monitoring center configured to compare the identified multiple arrhythmia events with a human assessment of a portion of the physiological data associated with a corresponding portion of the multiple arrhythmia events to determine that the multiple identified arrhythmia events, including events not in the human assessed portion of the data, are valid when a threshold of the multiple identified arrhythmia events identified by the mobile monitoring system matches events identified by the human assessment of the human assessed portion of the data, and the monitoring center further configured to output information for generation of a report to present the valid arrhythmia events with respect to a defined period of time.

9. The system of claim 8, wherein the monitoring center is further configured to provide the information over a network for displaying the report.

10. The system of claim 8, wherein the physiological data obtained by the sensor comprises ECG data.

11. The system of claim 10, wherein the multiple arrhythmia events comprise multiple atrial fibrillation events.

12. The system of claim 11, wherein the monitoring center is configured to output the information for generation of a pictographic report to present on a common time scale heart rate trend in alignment with indications of the valid arrhythmia events.

13. The system of claim 11, wherein the monitoring center is configured to output the information for generation of a pictographic report to present a range of heart rates and a heart rate average for each of multiple time intervals juxtaposed with an indication of intervals of the multiple time intervals that correspond to the valid events.

14. The system of claim 13, wherein the monitoring center is configured to output the information for generation of a report to display an indication of a time interval of the multiple time intervals having a maximum heart rate for the multiple time intervals.

15. A computer-readable medium encoding a computer program product operable to cause one or more data processing apparatus to perform operations comprising:
    obtaining data associated with multiple arrhythmia events identified, according to a computer implemented process, in a physiological signal for a living being;
    receiving a human assessment of a portion of the data associated with a corresponding portion of the multiple arrhythmia events identified in the physiological signal;
    determining that the multiple arrhythmia events identified in the physiological signal, including events not in the human assessed portion of the data, are valid when a threshold of the arrhythmia events identified according to the computer implemented process in the physiological signal in the human assessed portion of the data, match events identified by the human assessment of the human assessed portion of the data; and
    generating information for a report to present the valid arrhythmia events for a defined period of time.

16. The computer readable medium of claim 15, wherein obtaining the data associated with the multiple arrhythmia events identified according to the computer implemented process, in the physiological signal comprises obtaining ECG data.

17. The computer readable medium of claim 16, wherein generating the information for the report comprises generating information for a pictographic report presenting on a common time scale heart rate trend in alignment with indications of the valid arrhythmia events.

18. The computer readable medium of claim 16, wherein generating the information for the report comprises generating information for a pictographic report presenting a range of heart rates and a heart rate average for each of multiple time intervals juxtaposed with an indication of intervals of the multiple time intervals that correspond to the valid arrhythmia events.

19. The computer readable medium of claim 18, the operations further comprising providing the information over a network for displaying the report.

20. The computer readable medium of claim 18, wherein generating the information for the report comprises generating information for presenting on the pictographic report an indication of a time interval of the multiple time intervals having a minimum heart rate for the multiple time intervals.

21. The computer readable medium of claim 20, wherein generating the information for the report comprises generating information for presenting on the pictographic report an indication of a time interval of the multiple time intervals having a maximum heart rate for the multiple time intervals.

* * * * *